United States Patent [19]

Shuster et al.

[11] 4,040,987
[45] Aug. 9, 1977

[54] 2-ALKYL-SUBSTITUTED-4,5-DIMETHYL THIAZOLINE PERFUME AND COLOGNE COMPOSITIONS

[75] Inventors: Edward J. Shuster, Brooklyn, N.Y.; Donald Arthur Withycombe, Lincroft, N.J.; Braja Dulal Mookherjee, Holmdel, N.J.; Cynthia J. Mussinan, Bricktown, N.J.

[73] Assignee: International Flavors & Fragrances Inc., New York, N.Y.

[21] Appl. No.: 730,653

[22] Filed: Oct. 7, 1976

[51] Int. Cl.$^2$ .............................. C11B 9/00
[52] U.S. Cl. ............................ 252/522; 260/306.7 R; 426/534
[58] Field of Search ................. 252/522; 260/306.7 R

[56] References Cited
U.S. PATENT DOCUMENTS

| 2,865,924 | 12/1958 | Asinger et al. | 260/306.7 R |
| 2,879,273 | 3/1959 | Asinger et al. | 260/306.7 R |
| 2,886,571 | 5/1959 | Schade et al. | 260/306.7 R |
| 3,700,683 | 10/1972 | Asinger et al. | 260/306.7 R |
| 3,769,040 | 10/1973 | Pittet et al. | 252/522 |
| 3,876,652 | 4/1975 | Pittet et al. | 252/522 |
| 3,931,208 | 1/1976 | Offermaus et al. | 260/306.7 R |

OTHER PUBLICATIONS

Alan P. Pittet et al. *J. Agr. Food Chem.*, vol. 22, No. 2, pp. 264–269, 1974.
O. G. Vitzthum et al., *J. Food Sci.* 1210–1215, 1974.

*Primary Examiner*—Veronica O'Keefe
*Attorney, Agent, or Firm*—Arthur L. Liberman; Franklin D. Wolffe

[57] ABSTRACT

Perfume and fragrance compositions and perfumed articles including soaps, detergents, powders, as well as colognes containing 2-alkyl-substituted-4,5-dimethyl thiazolines having the structure:

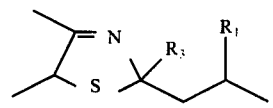

wherein $R_1$ and $R_3$ are the same or different, and each is selected from the group consisting of methyl and hydrogen, which impart thereto chocolate-like, fresh ground coffee-like, green, cucumber, dill aromas and yielding on dry-out floral, natural tuberose-like, orris-like nuances.

6 Claims, 7 Drawing Figures

FIG. 1

GC-MS PROFILE ISOMER I FOR EXAMPLE I

GC-MS PROFILE ISOMER II FOR EXAMPLE I

NMR SPECTRUM FOR EXAMPLE I
SOLVENT: CDCL₃
SWEEP WIDTH: 1000 Hz.

FIG. 4 I R SPECTRUM FOR EXAMPLE I

FIG. 5 GC-MS PROFILE FOR EXAMPLE II

FIG. 7

IR SPECTRUM FOR EXAMPLE II

2-ALKYL-SUBSTITUTED-4,5-DIMETHYL THIAZOLINE PERFUME AND COLOGNE COMPOSITIONS

BACKGROUND OF THE INVENTION

There is a continuing search for materials having desirable fragrance properties. Such materials are sought either to replace costly natural materials or to provide new fragrances or perfume types which have not heretofore been available. Especially desirable qualities for substances having interesting narcisse-type fragrances or cocoa aromas are stability and persistence, particularly in a wide variety of perfumed articles (e.g., soaps, detergents and powders), perfumed compositions and colognes, ease of manufacture and intensity of aroma.

Prior to the last decade it was the general opinion among those skilled in the art that compounds containing the thiazoline moiety having the structure:

were not desirable for use in conjunction with fragrance materials and perfumed articles such as soaps, detergents and powders. However, within the last decade, such thiazoles having an additional double bond have been found to be useful in perfumery. Thus, for example, in U.S. Pat. No. 3,769,040 issued on Oct. 30, 1973, compounds having the generic structure:

wherein R is hydrogen, alkyl or acyl, X is alkoxy, hydrogen or when R and Y are alkyl, alkyl; and Y is alkyl, acyl, alkoxy or hydrogen, no more than two of R, X and Y being hydrogen, impart a nut-like or vegetable-type aroma to perfumes, colognes and perfumed articles.

However, the nature and intensity and persistence of the aromas imparted by the thiazoline derivatives of the instant invention are different in kind and unexpectedly surprising when compared with the thiazole derivatives of U.S. Pat. No. 3,769,040.

THE INVENTION

The invention comprises novel compositions, perfumed articles and colognes containing 2-alkyl-substituted-4,5-dimethyl thiazolines having the structure:

wherein $R_1$ and $R_3$ are the same or different and each is selected from the group consisting of hydrogen and methyl; and processes for manufacturing such compositions, perfumed articles and colognes, the specific embodiments of which are described hereinafter by way of example and in accordance with which it is now preferred to practice the invention.

Briefly, the present invention provides the 2-alkyl-substituted-4,5-dimethyl thiazolines having the structure:

in perfume and fragrance modifying, augmenting or enhancing materials and perfumed articles including soaps, detergents and powders as well as colognes.

Such 2-alkyl-substituted-4,5-dimethyl thiazolines are obtained by reacting an aldehyde with aqueous ammonia to form the corresponding imine and then subsequently reacting the thus-formed imine with 2-mercapto-3-butanone to form the desired thiazoline derivative according to the following reaction sequence:

Details concerning the parameters of the above-mentioned reaction are exemplified hereinbelow and are also exemplified in the following publications:

German Auslegungschrift No. 1,058,061 published on May 27, 1959
U.S. Pat. No. 2,865,924 issued on Dec. 23, 1958
U.S. Pat. No. 2,879,273 issued on Mar. 24, 1959
German Auslegungschrift No. 1,068,717 published on Nov. 12, 1959
U.S. Pat. No. 3,700,683 issued on Oct. 24, 1972
German Auslegungschrift No. 1,095,284 published on Dec. 22, 1960
German Auslegungschrift No. 1,063,602 published on Aug. 20, 1959
U.S. Pat. No. 3,931,208 issued on Jan. 6, 1976
U.S. Pat. No. 2,886,571 issued on May 12, 1959.

Specific examples of the 2-alkyl-subsituted-4,5-dimethyl-$\Delta^3$-thiazolines using the aforementioned process and their perfumery properties are as follows (as set forth in Table I below):

| Compound | Structure | Perfumery Property |
| --- | --- | --- |
| 2n-propyl-2,4,5-trimethyl-Δ³-thiazoline |  | A green, cucumber, dill aroma yielding, on dry-out, floral, natural tuberose-like, and orris-like nuances. |
| 2(2'-methylpropyl)-4,5-dimethyl-Δ³-thiazoline | | An excellent fresh ground coffee aroma with deep green nuances |

One or more of the afore-mentioned 2-alkyl-substituted-4,5-dimethyl-Δ³-thiazolines having the structure:

wherein $R_1$ and $R_3$ are each the same or different and are each selected from the group consisting of hydrogen and methyl, is an olfactory agent and can be incorporated into a wide variety of compositions, each of which will be enhanced or augmented by its green, dill, coffee-like and/or floral, tuberose-like or orris-like nuances.

The 2-alkyl-substituted-4,5-dimethyl-Δ³-thiazolines can be added to perfume compositions as pure compounds or can be added to mixtures of materials in fragrance-imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciated that the 2-alkyl-substituted-4,5-dimethyl-Δ³-thiazoline(s) of our invention is(are) useful as olfactory agent(s) and fragrance(s).

The term "perfume composition" is used herein to mean a mixture of compounds, including, for example, natural oils, synthetic oils, alcohols, aldehydes, ketones, esters, lactones, nitriles and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation and (d) topnotes which are usually low-boiling, fresh-smelling materials. Such perfume compositions of our invention can be used in conjunction with carriers, vehicles, solvents, dispersants, emulsifiers, surface-active agents, aerosol propellants, and the like.

In perfume compositions the individual components contribute their particular olfactory characteristics, but the overall effect of the perfume composition will be the sum of the effect of each ingredient. Thus, one or more of the 2-alkyl-substituted-4,5-dimethyl-Δ³-thiazolines of our invention can be used to alter, augment, modify or enhance the aroma characteristics of a perfume composition or a perfumed article, for example, by highlighting or moderating the olfactory reaction contributed by another ingredient of the composition.

The amount of one or more of the 2-alkyl-substituted-4,5-dimethyl-Δ³-thiazolines of our invention which will be effective in perfume compositions depends upon many factors, including the other ingredients, their amounts and the effects which are desired. It has been found that perfume compositions containing as much as 2% or as little as 0.005% by weight of the mixtures or compounds of this invention, or even less can be used to impart intense deep green and coffee-like aromas and floral aromas to soaps, cosmetics and other products. The amount employed will depend upon considerations of cost, nature of the end products, the effect desired in the finished product, and the particular fragrance sought.

One or more of the 2-alkyl-substituted-4,5-dimethyl-Δ³-thiazolines of our invention as disclosed herein can be used alone, in a fragrance modifying composition, or in a perfume composition as an olfactory component in detergents (an anionic detergents, cationic detergents, and nonionic detergents) and soaps; space deodorants; perfumes, colognes, bath preparations such as bath oil, bath salts; hair preparations such as lacquers, brilliantines, pomades and shampoos; cosmetic preparations such as creams, deodorants, hand lotions, sun screens; powders such as talcs, dusting powders, face powders and the like. When one or more of the 2-alkyl-substituted-4,5-dimethyl-Δ³-thiazolines of our invention is used in perfumed articles such as the foregoing, it can be used in amounts of 0.01% or lower. Generally it is preferred not to use more than about 2% in the finished perfumed article, since the use of too much will tend to unbalance the total aroma and will needlessly raise the cost of the article.

The following examples serve to illustrate embodiments of the invention as it is now preferred to practice it. It will be understood that these examples are illustrative and the invention is to be considered restricted thereto only as indicated in the appended claims.

EXAMPLE I

Preparation of 2-(2'-Methyl-n-Propyl)-4,5-Dimethyl-Δ³-Thiazoline

Reaction:

Into a 500 ml, three-necked, round-bottom flask equipped with stirrer, 250 ml addition funnel, ice bath and Fredericks condenser, is placed 45 ml water and 45 ml water and 45 ml 58% aqueous $NH_3$. With stirring, 43 grams of isobutyraldehyde is added dropwise. 104 Grams of a 50% ethanolic solution of 3-mercapto-2-butanone is then added dropwise over a period of 1 hour. The reaction mass is then allowed to stir for 1 hour at room temperature.

The resulting product is extracted with three 100 ml portions of diethyl ether. The ether extracts are combined and dried over anhydrous sodium sulfate and then evaporated on a rotary evaporator. The resulting product is then distilled on a 12 inch Vigreux column at 4 mm Hg pressure and 70° C vapor temperature yielding a product containing 97% 2-(2'-methyl-n-propyl)-4,5-dimethyl-Δ³-thiazoline.

Figure 1:
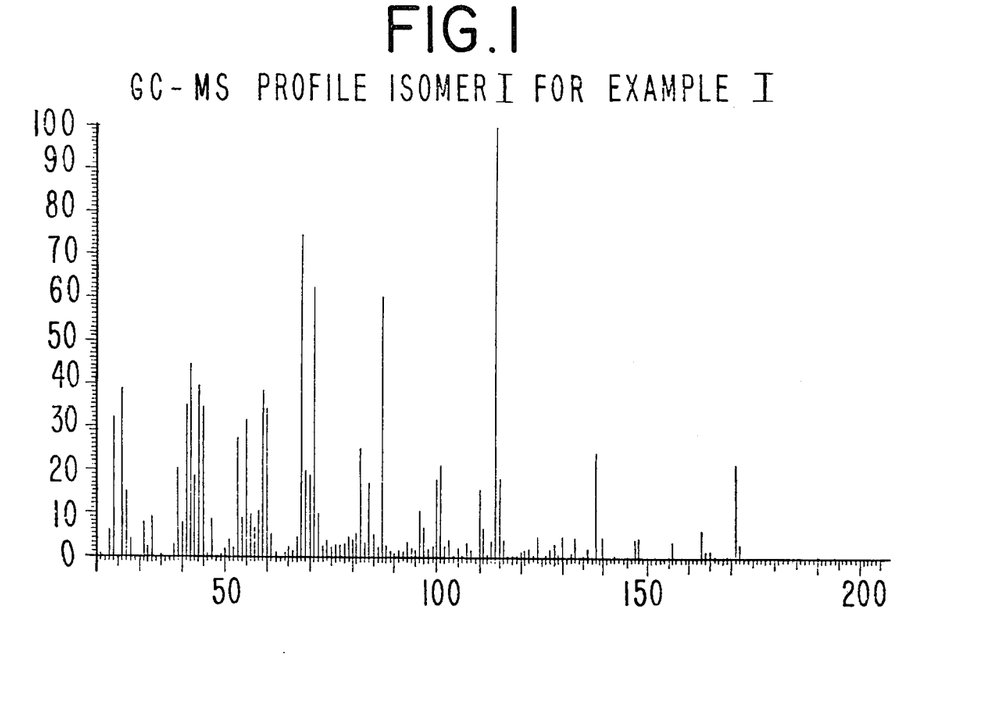
FIG. 1 represents the MS profile for a first isomer of 2(2'-methyl-n-propyl)-4,5-dimethyl-Δ³-thiazoline produced according to Example I.
Figure 2:
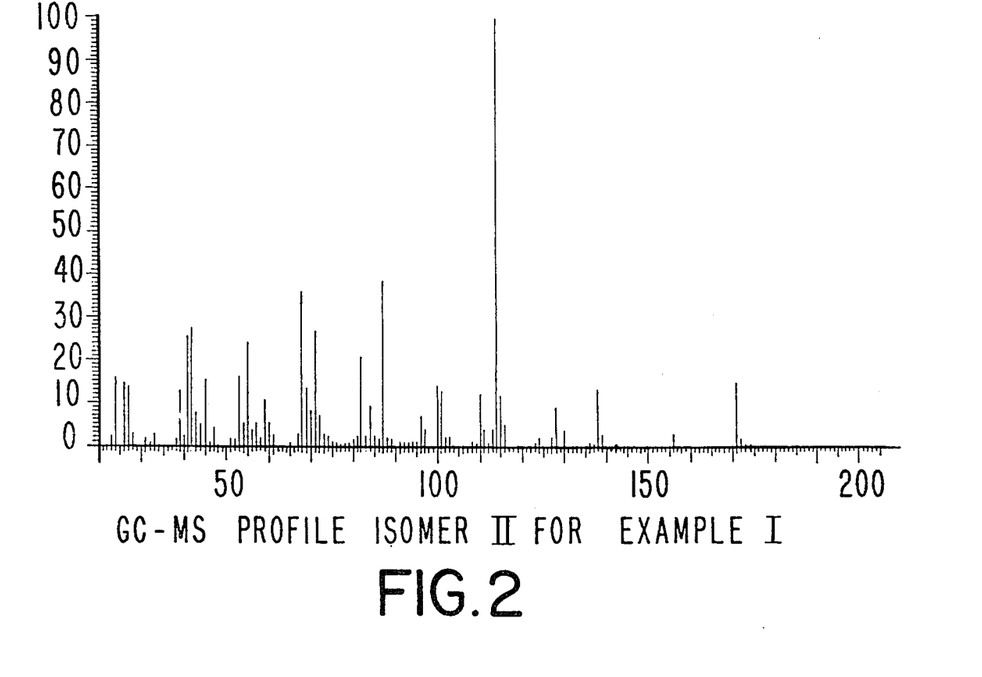
FIG. 2 represents the MS profile of a second isomer of 2(2'-methyl-n-propyl)-4,5-dimethyl-Δ³-thiazoline produced according to Example I.

The MS profiles show that two isomers exist; an "endo" and an "exo" isomer. The MS profile for isomer I is set forth in FIG. 1. The MS profile for isomer II is set forth in FIG. 2.

Figure 3:
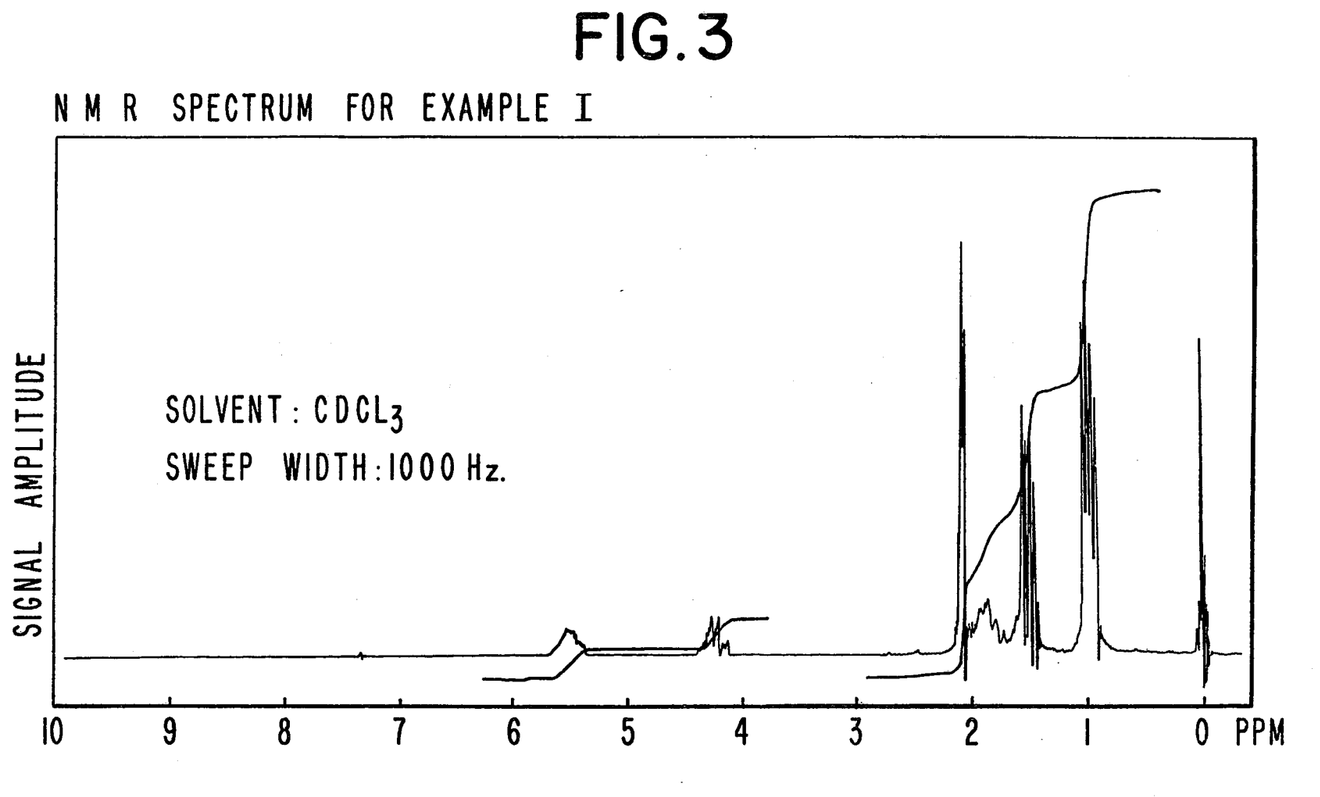
FIG. 3 represents the NMR spectrum for 2(2'-methyl-n-propyl)-4,5-dimethyl-Δ³-thiazoline produced according to Example I.

The NMR spectrum for the resulting product is set forth in FIG. 3.

Figure 4:
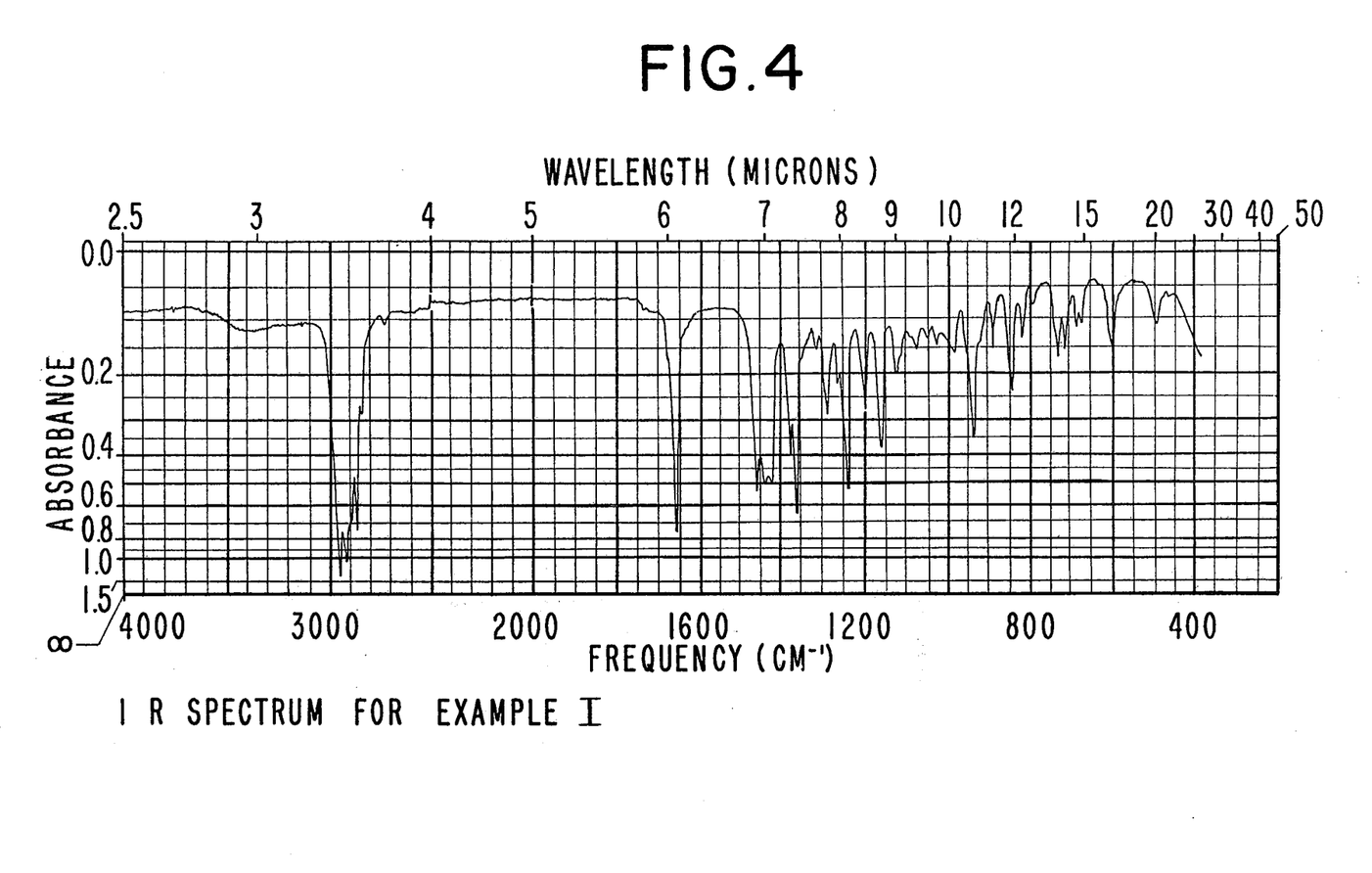
FIG. 4 represents the infrared spectrum for 2(2'-methyl-n-propyl)-4,5-dimethyl-Δ³-thiazoline produced according to Example I.

The infrared spectrum for the resulting product is set forth in FIG. 4.

The NMR analysis is as follows:

| Chemical Shift | Assignment | Protons |
|---|---|---|
| 1.00 ppm (doublet of doublets) | "Isopropyl" methyl protons | 6H |
| 1.50 (doublet of doublets) | $CH_3-\underset{\underset{C=N-}{\|}}{C}-S-$ | 3H |
| 2.10 (d, J=2H₂) | $CH_3-C=N-$ | 3H |
| 2.00–1.60 (m) | $-CH_2- + H-\underset{\|}{\overset{\|}{C}}-$ | 3H |
| 4.25 (m) | $\underset{\underset{C=N-}{\|}}{HC}-S$ | 1H |

-continued

| Chemical Shift | Assignment | Protons |
|---|---|---|
| 5.55 (m) | $\underset{\underset{S-}{\|}}{HC}-N=C=$ | 1H |

The IR analysis is as follows: 940 cm⁻¹, 1160, 1200, 1370, 1380, 1430, 1440, 1470, 1670, 2880, 2940, 2960.

The mass spectral analysis is as follows:

| M/E | Relative Intensity |
|---|---|
| 41 | 15 |
| 42 | 19 |
| 55 | 17 |
| 68 | 54[2] |
| 71 | 36[5] |
| 87 | 43[3] |
| 101 | 19 |
| 114 | 100[1] |
| 138 | 30[6] |
| M 171 | 40[4] |

EXAMPLE II

Preparation of 2,4,5-Trimethyl-2-n-Propyl-Δ³-Thiazolene

Reaction:

Into a 500 ml, three-necked, round-bottom flask equipped with mechanical stirrer, 250 ml addition funnel, thermometer, Frederick condenser and ice bath is placed 45.2 ml of a 58% aqueous $NH_3$ solution and 45 ml distilled water. 43.05 Grams of 2-pentanone is then added dropwise from the addition funnel with stirring while maintaining the reaction mass at a temperature of between 25° and 28° C. At the completion of the addition of the 2-pentanone, 104 grams of a 50% (in 95% ethanol) solution of 3-mercapto-2-butanone is then added to the reaction mass over a period of 1 hour with stirring while maintaining the reaction mass at room temperature. The reaction mass is then extracted with three 100 ml portions of diethyl ether, and the diethyl ether extracts are combined. The ether extracts are then washed with two 100 ml portions of water, and the ether extracts are dried over anhydrous sodium sulfate and evaporated on a rotary evaporator. The resulting product is then distilled at a vapor temperature of 104° C and a pressure of 31 mm Hg.

Figure 5:
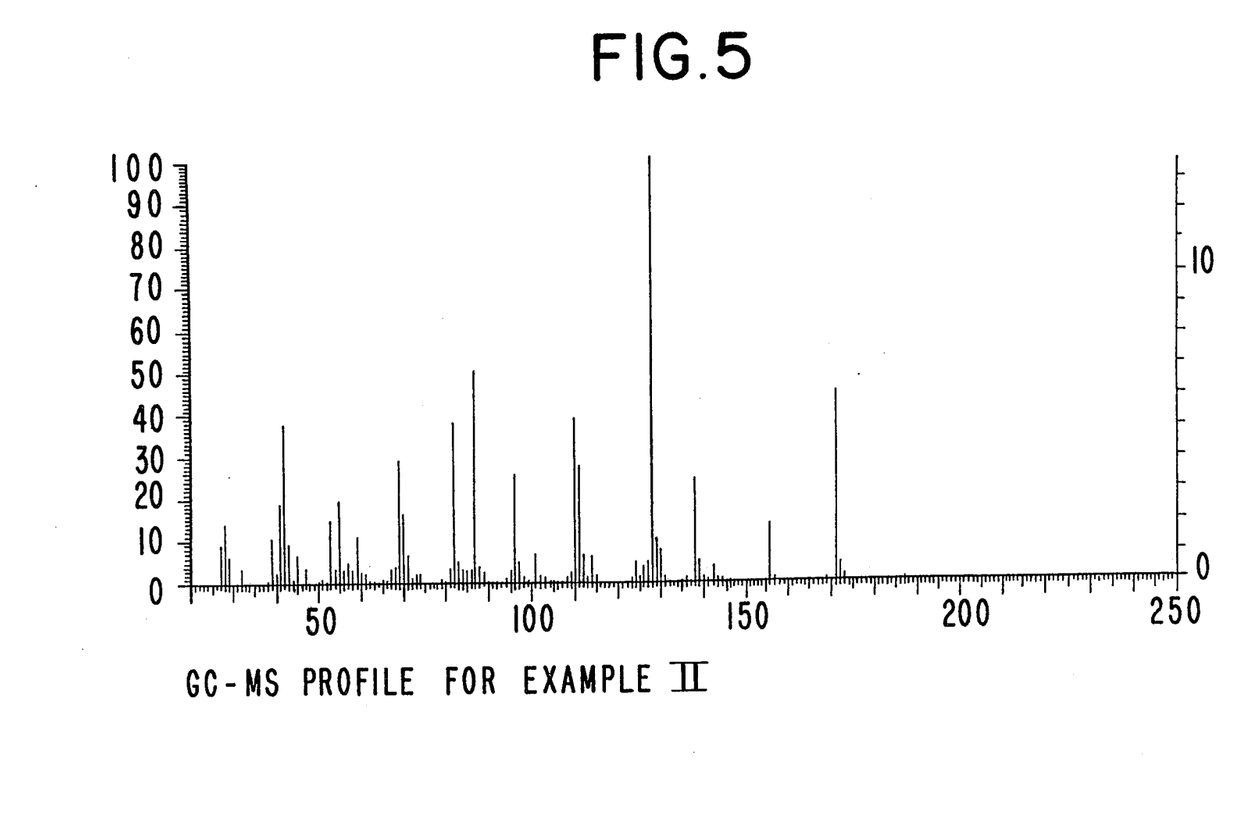
FIG. 5 represents the MS profile for 2-n-propyl-2,4,5-trimethyl-Δ³-thiazoline produced according to Example II.

The MS profile of the resulting material is set forth in FIG. 5.

Figure 6:
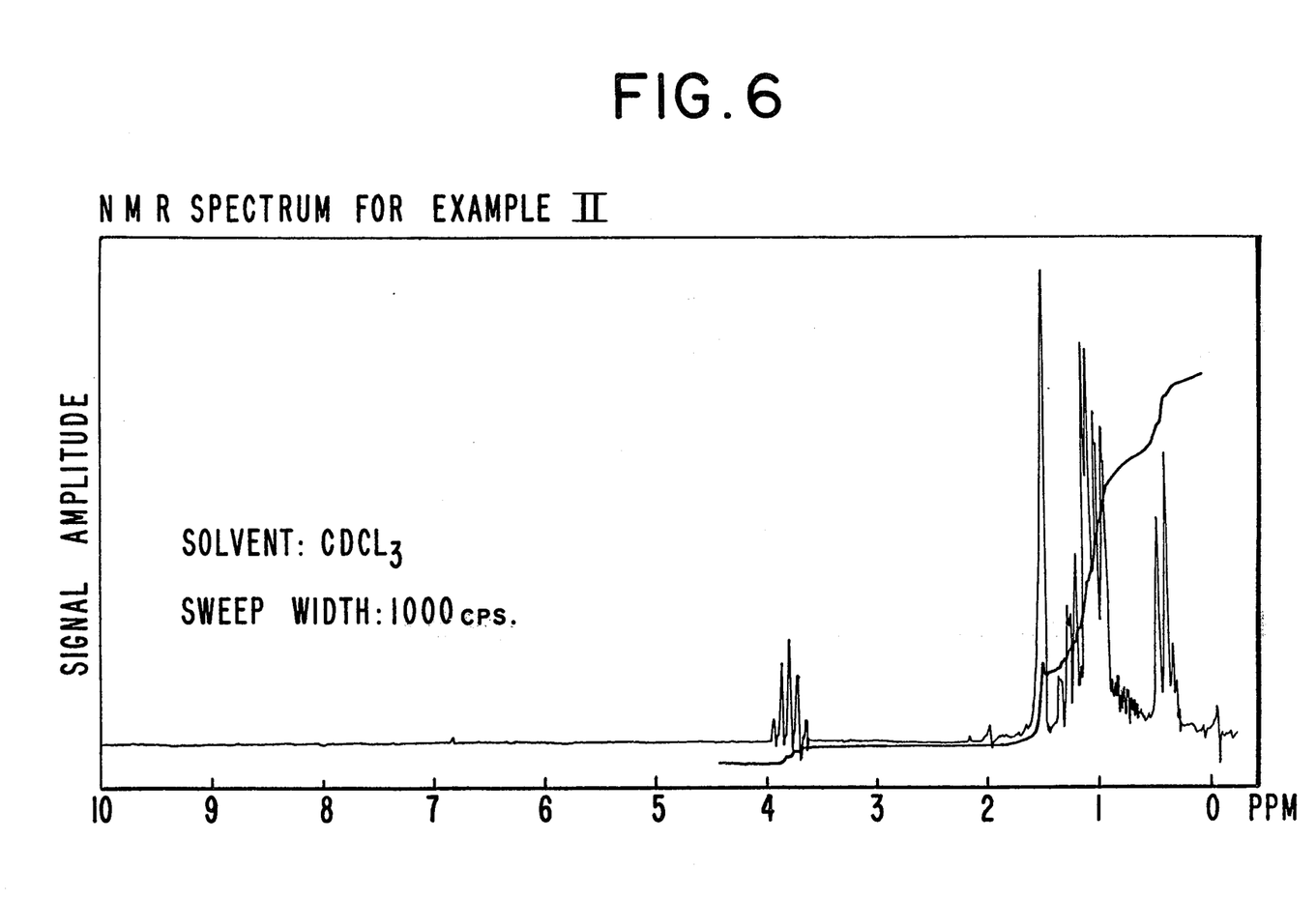
FIG. 6 represents the NMR spectrum for 2n-propyl-2,4,5-trimethyl-Δ³-thiazoline produced according to Example II.

The NMR spectrum of the resulting material is set forth in FIG. 6.

Figure 7:
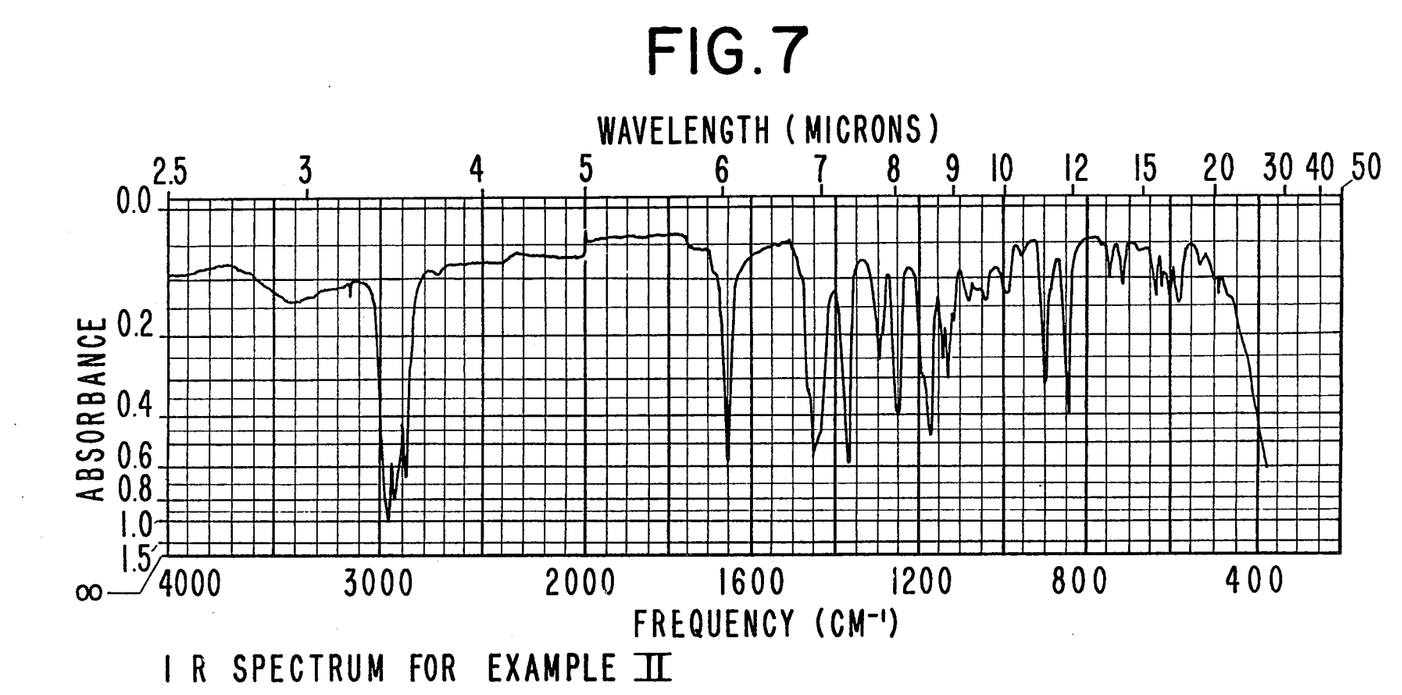
FIG. 7 represents the infrared spectrum for 2n-propyl-2,4,5-trimethyl-Δ³-thiazoline produced according to Example II.

The infrared spectrum of the resulting material is set forth in FIG. 7.

The NMR spectrum analysis is set forth as follows:

| Chemical Shift (ppm) | Assignment | Quantification |
|---|---|---|
| 0.90 | $CH_3-$ | 3H |
| 1.48 | $CH_3-C-S$ | |
| 1.58 | | 10H |
| | $CH_3-C-N=$ | |
| 1.84–1.11 | $-CH_2-$ | |
| 2.02 | $CH_3-C=N-$ | 3H |
| 4.26 | $CH_3-CH-S-$ | 1H |

The infrared analysis is as follows: 840 cm$^{-1}$, 895, 1130, 1180, 1250, 1370, 1450, 1670, 2880, 2940, 2960.

The mass spectral analysis is as follows:

| M/E | Relative Intensity |
|---|---|
| 42 | 31$^6$ |
| 69 | 24 |
| 82 | 34$^5$ |
| 87 | 44$^2$ |
| 96 | 22 |
| 110 | 34$^4$ |
| 111 | 22 |
| 128 | 100$^1$ |
| 138 | 25 |
| M 171 | 40$^3$ |

EXAMPLE III

Narcisse Perfume Formulation

The following formulation is prepared:

| Ingredients | Parts by Weight |
|---|---|
| 2-(2'-methylpropyl)-4,5-dimethyl-$\Delta^3$-thiazoline | 3 |
| Heliotropine | 30 |
| Para cresyl phenyl acetate | 15 |
| Oxyphenylon | 1 |
| Para cresol | 2 |
| Acetyl isoeugenol | 20 |
| Isoeugenol | 15 |
| Ylang extra | 5 |
| Nerol | 50 |
| Geraniol | 40 |
| Terpinenol 4 | 5 |
| α-terpinineol | 35 |
| Linalool (synthetic) | 50 |
| Benzyl alcohol | 80 |
| Benzyl acetate | 10 |
| Para cresyl salicylate | 50 |

The 2-(2'-methylpropyl)-4,5-dimethyl-$\Delta^3$-thiazoline imparts a deep green, coffee-like note so necessary for the Narcisse formulation.

EXAMPLE IV

Preparation of a Soap Composition

100 Grams of soap chips are mixed with one gram of the composition produced according to Example III until a substantially homogeneous composition is obtained. The perfumed soap composition manifests an excellent Narcisse aroma having deep green and coffee-like nuances.

EXAMPLE V

Preparation of a Detergent Composition

A total of 100 grams of a detergent powder prepared according to Example I of Canadian Pat. No. 895,597 issued on Mar. 16, 1976, is intimately admixed with 0.15 grams of the perfume composition prepared according to Example III until a substantially homogeneous composition is obtained. This composition has an excellent Narcisse aroma with deep green and coffee-like nuances.

EXAMPLE VI

Preparation of Cosmetic Powder Composition

A cosmetic powder is prepared by mixing in a ball mill 100 grams of talcum powder with 0.25 grams of the Narcisse formulation prepared according to Example III. The resulting powder has an excellent Narcisse aroma having, in addition, deep green and coffee-like nuances.

EXAMPLE VII

Perfumed Liquid Detergent

Concentrated liquid detergents with rich, pleasant, Narcisse aromas are prepared containing 0.10, 0.15 and 0.20% of the Narcisse formulation of Example III. They are prepared by adding and homogeneously admixing the appropriate quantity of the product of Example III in the liquid detergent. The liquid detergents are all produced using anionic detergents containing a 50:50 mixture of sodium lauroyl sarcosinate and potassium N-methyl lauroyl tauride. The detergents all possess a pleasant fragrance which can be described as Narcisse having deep green and coffee-like nuances.

EXAMPLE VIII

Cologne and Handkerchief Perfume

The composition of Example III is incorporated into a cologne at a concentration of 2.5% in 85% aqueous ethanol; and into a handkerchief perfume at a concentration of 25% (in 95% aqueous ethanol). A distinct and definite strong Narcisse fragrance is imparted to the cologne and to the handkerchief perfume, and these fragrances have intense and pleasant underlying deep green and coffee-like nuances.

EXAMPLE IX

Cologne and Handkerchief Perfume 2n-propyl-2,4,5-trimethyl-$\Delta^3$-thiazoline produced according to Example II is incorporated into a cologne at a concentration of 2.5% in 85% aqueous ethanol; and into a handkerchief perfume at a concentration of 20% (in 95% aqueous ethanol). A distinct and definite strong green, floral fragrance having tuberose-like and orris-like nuances is imparted to the cologne and to the handkerchief perfume.

EXAMPLE X

Cologne and Handkerchief Perfume

2(2'-methylpropyl)-4,5-dimethyl-$\Delta^3$-thiazoline produced according to Example I is incorporated into a cologne at a concentration of 2.5% in 85% aqueous ethanol; and into a handkerchief perfume at a concentration of 20% (in 95% aqueous ethanol). A distinct and definite strong coffee-like fragrance with excellent green nuances is imported to the cologne and to the handkerchief perfume.

What is claimed is:

1. A perfumed composition comprising a perfuming quantity of a 2-alkyl-substituted-4,5-dimethyl thiazoline having the structure:

wherein $R_1$ and $R_3$ are the same or different and each is selected from the group consisting of hydrogen and methyl, and at least one adjuvant selected from the group consisting of natural perfume oils, synthetic perfume oils, alcohols, aldehydes, ketones, nitriles, esters and lactones.

2. A cologne comprising ethanol, water and a 2-alkyl-substituted-4,5-dimethyl-$\Delta^3$-thiazoline having the structure:

wherein $R_1$ and $R_3$ are the same or different and each is selected from the group consisting of methyl and hydrogen.

3. The composition of claim 1, wherein in the thiazoline compound, $R_1$ is hydrogen and $R_3$ is methyl.

4. The composition of claim 1, wherein in the thiazoline compound, $R_1$ is methyl and $R_3$ is hydrogen.

5. A cologne of claim 2, wherein in the thiazoline compound $R_1$ is hydrogen and $R_3$ is methyl.

6. A cologne of claim 2, wherein in the thiazoline compound $R_1$ is methyl and $R_3$ is hydrogen.

* * * * *